US009128860B2

(12) United States Patent
Sequera

(10) Patent No.: US 9,128,860 B2
(45) Date of Patent: Sep. 8, 2015

(54) METHOD OF IMAGING REAGENT BEADS, ANALYZING, AND REDISTRIBUTING INTENSITY

(75) Inventor: Dean Eric Sequera, Vienna, VA (US)

(73) Assignee: Dynex Technologies, Inc., Chantilly, VA (US)

( * ) Notice: Subject to any disclaimer, the term of this patent is extended or adjusted under 35 U.S.C. 154(b) by 0 days.

(21) Appl. No.: 14/113,180

(22) PCT Filed: Apr. 20, 2012

(86) PCT No.: PCT/IB2012/052012
§ 371 (c)(1),
(2), (4) Date: Oct. 21, 2013

(87) PCT Pub. No.: WO2012/143909
PCT Pub. Date: Oct. 26, 2012

(65) Prior Publication Data
US 2014/0052382 A1    Feb. 20, 2014

(30) Foreign Application Priority Data

| Apr. 20, 2011 | (GB) | 1106699.0 |
| Jun. 16, 2011 | (EP) | 11170128 |
| Jun. 16, 2011 | (GB) | 1110178.9 |
| Mar. 21, 2012 | (GB) | 1204935.9 |

(51) Int. Cl.
| G01N 33/48 | (2006.01) |
| G06F 19/10 | (2011.01) |
| G06F 19/20 | (2011.01) |
| G01N 33/50 | (2006.01) |
| G06K 9/00 | (2006.01) |
| G06K 9/40 | (2006.01) |
| G06K 9/36 | (2006.01) |
| G06F 19/24 | (2011.01) |

(52) U.S. Cl.
CPC ............... *G06F 19/10* (2013.01); *G06F 19/20* (2013.01); *G06F 19/24* (2013.01)

(58) Field of Classification Search
None
See application file for complete search history.

(56) References Cited

U.S. PATENT DOCUMENTS

2008/0090735 A1    4/2008    Le Cocq et al.

FOREIGN PATENT DOCUMENTS

| WO | WO 02/06854 | 1/2002 |
| WO | WO 2009/146036 | 12/2009 |
| WO | WO 2011/012859 | 2/2011 |
| WO | WO 2012/013959 | 2/2012 |

OTHER PUBLICATIONS

Lin, "A Multi-Model Approach to Simultaneous Segmentation and Classification of Heterogeneous Populations of Cell Nuclei in 3D Confocal Microscope Images," Cytometry Part A, vol. 71A, p. 724-736, 2007.*
Shutin et al., "*Application of Information-Theoretic Measures to Quantitative Analysis of Immunofluorescent Microscope Imaging*", Computer Methods and Programs in Biomedicine, Elsevier, vol. 97, No. 2, Feb. 1, 2010, pp. 114-129.

* cited by examiner

*Primary Examiner* — Eric S Dejong
*Assistant Examiner* — G. Steven Vanni
(74) *Attorney, Agent, or Firm* — Diederiks & Whitelaw, PLC

(57) ABSTRACT

A method of analyzing reagent beads retained in a sample well of a sample plate is disclosed comprising obtaining an image of a reagent bead, distributing intensity values of image pixels amongst a plurality of intensity bins and generating an histogram. A curve is fitted to the histogram and the curve is compared with an idealized profile of image pixels. A closeness of fit between the curve and the idealized profile is determined and then intensity values are discarded from one or more of the intensity bins. The remaining intensity values are redistributed and the process is repeated several times. A determination is then made as to which curve has the closest fit with the idealized profile.

8 Claims, 13 Drawing Sheets

METHOD OF IMAGING REAGENT BEADS, ANALYZING, AND REDISTRIBUTING INTENSITY

CROSS-REFERENCE TO RELATED APPLICATIONS

This application represents a National Stage application of PCT/IB2012/052012 entitled "Method of Analysing Reagent Beads" filed Apr. 20, 2012, pending.

BACKGROUND OF THE INVENTION

The present invention relates to a method of analysing reagent beads and an analyser for analysing reagent beads.

It is known to dispense millimeter sized reagent beads, macrobeads or macrospheres into a sample plate in order to carry out diagnostic testing such as Enzyme Linked ImmunoSorbent Assay ("ELISA") procedures or other immunoassay procedures. Alternatively, the sample plate may be used to carry out testing for DNA or RNA sequences.

Immunoassay procedures are a preferred way of testing biological products. These procedures exploit the ability of antibodies produced by the body to recognise and combine with specific antigens which may, for example, be associated with foreign bodies such as bacteria or viruses, or with other body products such as hormones. Once a specific antigen-antibody combination has occurred it can be detected using chromogenic, fluorescent or chemiluminescent materials or less preferably by using radioactive substances. Radioactive substances are less preferred due to environmental and safety concerns regarding their handling, storage and disposal. The same principles can be used to detect or determine any materials which can form specific binding pairs, for example using lectins, rheumatoid factor, protein A or nucleic acids as one of the binding partners.

ELISA is a particularly preferred form of immunoassay procedure wherein one member of the binding pair is linked to an insoluble carrier surface ("the solid phase") such as a sample vessel, and after reaction the bound pair is detected by use of a further specific binding agent conjugated to an enzyme ("the conjugate"). The procedures for ELISA are well known in the art and have been in use for both research and commercial purposes for many years. Numerous books and review articles describe the theory and practice of immunoassays. Advice is given, for example, on the characteristics and choice of solid phases for capture assays, on methods and reagents for coating solid phases with capture components, on the nature and choice of labels, and on methods for labelling components. An example of a standard textbook is "ELISA and Other Solid Phase Immunoassays, Theoretical and Practical Aspects", Editors D. M. Kemeny & S. J. Challacombe, published by John Wiley, 1988. Such advice may also be applied to assays for other specific binding pairs.

In the most common type of ELISA, the solid phase is coated with a member of the binding pair. An aliquot of the specimen to be examined is incubated with the solid coated solid phase and any analyte that may be present is captured onto the solid phase. After washing to remove residual specimen and any interfering materials it may contain, a second binding agent, specific for the analyte and conjugated to an enzyme is added to the solid phase. During a second incubation any analyte captured onto the solid phase will combine with the conjugate. After a second washing to remove any unbound conjugate, a chromogenic substrate for the enzyme is added to the solid phase. Any enzyme present will begin to convert the substrate to a chromophoric product. After a specified time the amount of product formed may be measured using a spectrophotometer, either directly or after stopping the reaction.

It will be realised that the above is an outline description of a general procedure for bioassay and that many variants are known in the art including fluorogenic and luminogenic substrates for ELISA, direct labelling of the second member of the binding pair with a fluorescent or luminescent molecule (in which case the procedure is not called an ELISA but the process steps are very similar) and nucleic acids or other specific pairing agents instead of antibodies as the binding agent. However, all assays require that fluid samples, e.g. blood, serum, urine, etc., are aspirated from a sample tube and are then dispensed into a solid phase. Samples may be diluted prior to being dispensed into the solid phase or they may be dispensed into deep well microplates, diluted in situ and then the diluted analyte may be transferred to the functional solid phase.

The most common type of solid phase is a standard sample vessel known as a microplate which can be stored easily and which may be used with a variety of biological specimens. Microplates have been available commercially since the 1960s and are made from e.g. polystyrene, PVC, Perspex or Lucite and measure approximately 5 inches (12.7 cm) in length, 3.3 inches (8.5 cm) in width, and 0.55 inches (1.4 cm) in depth. Microplates made from polystyrene are particularly preferred on account of polystyrene's enhanced optical clarity which assists visual interpretation of the results of any reaction. Polystyrene microplates are also compact, lightweight and easily washable. Microplates manufactured by the Applicants are sold under the name "MICROTITRE"®. Known microplates comprise 96 wells (also commonly known as "microwells") which are symmetrically arranged in an 8×12 array. Microwells typically have a maximum volume capacity of approximately 350 µl. However, normally only 10-200 µl of fluid is dispensed into a microwell. In some arrangements of the microplate the microwells may be arranged in strips of 8 or 12 wells that can be moved and combined in a carrier to give a complete plate having conventional dimensions.

Positive and negative controls are generally supplied with commercial kits and are used for quality control and to provide a relative cut-off. After reading the processed microplate, the results of the controls are checked against the manufacturer's validated values to ensure that the analysis has operated correctly and then the value is used to distinguish positive from negative specimens and a cut-off value is calculated. Standards are usually provided for quantitative assays and are used to build a standard curve from which the concentration of analyte in a specimen may be interpolated.

It will be recognised that the ELISA procedure as outlined above involves multiple steps including pipetting, incubation, washing, transferring microplates between activities, reading and data analysis. In recent years systems have been developed which automate the steps (or "phases") involved in the ELISA procedures such as sample distribution, dilution, incubation at specific temperatures, washing, enzyme conjugate addition, reagent addition, reaction stopping and the analysis of results. The pipette mechanism used to aspirate and dispense fluid samples uses disposable tips which are ejected after being used so as to prevent cross-contamination of patients' samples. Multiple instrumental controls are in place to ensure that appropriate volumes, times, wavelengths and temperatures are employed, data transfer and analysis is fully validated and monitored. Automated immunoassay apparatus for carrying out ELISA procedures are now widely used in laboratories of e.g. pharmaceutical companies, veterinary and botanical laboratories, hospitals and universities for in-vitro diagnostic applications such as testing for diseases and infection, and for assisting in the production of new vaccines and drugs.

ELISA kits are commercially available which consist of microplates having microwells which have been coated by the manufacturer with a specific antibody (or antigen). For example, in the case of a hepatitis B antigen diagnostic kit, the kit manufacturer will dispense anti-hepatitis B antibodies which have been suspended in a fluid into the microwells of a microplate. The microplate is then incubated for a period of time, during which time the antibodies adhere to the walls of the microwells up to the fluid fill level (typically about half the maximum fluid capacity of the microwell). The microwells are then washed leaving a microplate having microwells whose walls are uniformly covered with anti-hepatitis B antibodies up to the fluid fill level.

A testing laboratory will receive a number of sample tubes containing, for example, body fluid from a number of patients. A specified amount of fluid is then aspirated out of the sample tube using a pipette mechanism and is then dispensed into one or more microwells of a microplate which has been previously prepared by the manufacturer as discussed above. If it is desired to test a patient for a number of different diseases then fluid from the patient must be dispensed into a number of separate microplates, each coated by its manufacturer with a different binding agent. Each microplate can then be processed separately to detect the presence of a different disease. It will be seen that to analyse several different analytes requires a multiplicity of microplates and transfer of aliquots of the same specimen to the different microplates. This leads to large numbers of processing steps and incubators and washing stations that can cope with many microplates virtually simultaneously. In automated systems this requires instruments to have multiple incubators and complex programming is required to avoid clashes between microplates with different requirements. For manual operation either several technicians are required or the throughput of specimens is slow. It is possible to combine strips of differently coated microwells into a single carrier, add aliquots of a single specimen to the different types of well and then perform the ELISA in this combined microplate. Constraints on assay development, however, make this combination difficult to achieve and it is known in the art that for users to combine strips in this fashion can lead to errors of assignment of result, while manufacture of microplates with several different coatings in different microwells presents difficulties of quality control.

Conventional ELISA techniques have concentrated upon performing the same single test upon a plurality of patient samples per microplate or in detecting the presence of one or more of a multiplicity of analytes in those patients without distinguishing which of the possible analytes is actually present. For example, it is commonplace to determine in a single microwell whether a patient has antibodies to HIV-1 or HIV-2, or HIV-1 or -2 antigens, without determining which analyte is present and similarly for HCV antibodies and antigens.

However, a new generation of assays are being developed which enable multiplexing to be performed. Multiplexing enables multiple different tests to be performed simultaneously upon the same patient sample.

A recent approach to multiplexing is to provide a microplate comprising 96 sample wells wherein an array of different capture antibodies is disposed in each sample well. The array comprises an array of 20 nl spots each having a diameter of 350 µm. The spots are arranged with a pitch spacing of 650 µm. Each spot corresponds with a different capture antibody.

Multiplexing enables a greater number of data points and more information per assay to be obtained compared with conventional ELISA techniques wherein each sample plate tests for a single analyte of interest. The ability to be able to combine multiple separate tests into the same assay can lead to considerable time and cost savings. Multiplexing also enables the overall footprint of the automated apparatus to be reduced.

Although there are many advantageous aspects to current known ELISA techniques and to the new multiplex techniques which are currently being developed, it is nonetheless desired to provide a sample plate and associated automated apparatus which has an improved format and which provides a greater flexibility than state of the art ELISA arrangements.

In addition to ELISA procedures it is also known to use a hybridization probe to test for the presence of DNA or RNA sequences. A hybridization probe typically comprises a fragment of DNA or RNA which is used to detect the presence of nucleotide sequences which are complementary to the DNA or RNA sequence on the probe. The hybridization probe hybridizes to single-stranded nucleic acid (e.g. DNA or RNA) whose base sequence allows pairing due to complementarity between the hybridization probe and the sample being analysed. The hybridization probe may be tagged or labelled with a molecular marker such as a radioactive or more preferably a fluorescent molecule. The probes are inactive until hybridization at which point there is a conformational change and the molecule complex becomes active and will then fluoresce (which can be detected under UV light) DNA sequences or RNA transcripts which have a moderate to high sequence similarity to the probe are then detected by visualising the probe under UV light.

Macrobead multiplexing technology is currently being developed wherein millimeter sized reagent beads coated with an antigen or antibody are embedded in a single sample well such that samples can be tested against multiple analytes at the same time. It will be apparent that the size and characteristics of the millimeter sized macrobeads is quite different from other technologies involving micron sized beads.

Macrobeads and sample plates which are the subject of the present invention are disclosed in WO2011/012859 and WO2012/013959 the entire contents of which are incorporated herein by reference.

At the end of a test procedure the reagent beads in a sample well are analysed by determining the intensity of a chemiluminescent, chromogenic or fluorescent indicator present on each bead. The indicator is indicative of the specific binding for that analyte. However, since the reagent beads are in relatively close proximity to each other then light from other reagent beads may be directly reflected off a particular reagent bead (or indirectly off the sample well wall) and will be directed towards the camera detector or imaging sensor. As a result, the determined intensity associated with the particular reagent bead may be affected by direct reflections from a neighbouring reagent bead or indirectly through reflections from the sample well wall. Deformities in the surface of a reagent bead may also cause an abnormal concentration of signal due to light redirection or an accumulation of materials that may not have been sufficiently removed in previous wash steps.

WO02/06854 discloses a method of evaluating the signal intensity of an area of a substrate. A scatter parameter of the substrate is determined and the scatter effect is mathematically corrected. The disclosure teaches a method of seeking to identify pixels which belong to two distinct groups i.e. background and signal. It is assumed that these two distinct groups are each made up of a population than can be characterised by a normal distribution.

However, the disclosed method is not suitable for use when seeking to analyse reagent beads or macrobeads located in a sample well of a sample plate. In particular, the effects of direct reflection from light emitted from an adjacent bead and from well walls, irregularities in the surface of beads which result in residue build-up, irregular pockets of residue surrounding the beads and the spherical shape of the beads results in an irregular distribution of analyte signal which does not have a normal distribution.

The method disclosed in WO02/06854 is not, therefore, suitable for seeking to analyse reagent beads or macrobeads located in a sample well of a sample plate.

It is desired to provide an improved method of analysing reagent beads or macrobeads in a sample well of a sample plate.

SUMMARY OF THE INVENTION

According to an aspect of the present invention there is provided a method of analysing one or more reagent beads or macrobeads retained or secured in a sample well of a sample plate, the method comprising:

(i) obtaining an image of a reagent bead or macrobead, the image comprising a plurality of image pixels each having an associated intensity value;

(ii) distributing the intensity values or values related to the intensity values of the image pixels amongst a plurality of intensity bins and generating an histogram;

(iii) fitting a curve to the histogram;

(iv) comparing the curve with an idealised profile of image pixels which may be expected to be observed if an image of a reagent bead or macrobead which was unaffected by light emanating from neighbouring reagents beads or macrobeads were analysed;

(v) determining a closeness of fit between the curve and the idealised profile;

(vi) discarding intensity values or values related to the intensity values from one or more of the intensity bins and redistributing the remaining intensity values or values related to the intensity values amongst a plurality of intensity bins and generating a further histogram;

(vii) repeating steps (iii)-(vi) a plurality of times;

(viii) determining which curve has the closest fit with the idealised profile; and (ix) determining the intensity of the reagent bead or macrobead by using or summing the intensity values or values related to the intensity values which were not discarded and which were distributed amongst the plurality of intensity bins which gave the curve having the closest fit with the idealised profile.

According to the preferred embodiment "values related to the intensity values" relates to using a logarithm of the intensity values. However, other embodiments are also contemplated. For example, a fixed background value may be subtracted from each of the intensity values and hence the phrase "values related to the intensity values" may also relate to intensity values which have been corrected or which are otherwise related to the intensity values but which are not necessarily a logarithm of the intensity values.

According to an embodiment the reagent beads or macrobeads preferably have a size or diameter of 0.5-1.0 mm, 1.0-1.5 mm, 1.5-2.0 mm, 2.0-2.5 mm, 2.5-3.0 mm, 3.0-3.5 mm, 3.5-4.0 mm, 4.0-4.5 mm, 4.5-5.0 mm and >5.0 mm. The spherical reagent beads or macrobeads are preferably inserted in bores which preferably have a circular cross-section in the sample plate. The reagent beads or macrobeads once inserted into the bores in a sample well of a sample plate preferably form a substantially fluid tight circumferential seal with the wall of the bores. As a result, fluid is substantially prevented from passing down a bore in the sample well past or around a reagent or macrobead.

The step of distributing the intensity values preferably comprises:

determining a logarithm of the intensity values; and
distributing the logarithm of the intensity values amongst a plurality of intensity bins and generating a first histogram.

According to an embodiment either:

(i) the logarithm comprises a binary, natural or common logarithm; or (ii) the base of the logarithm has a value 2, e or 10; or (iii) the base of the logarithm has a value in the range 2-10 or 10-20 or >20.

According to an embodiment:

(i) the curve comprises a 4th, 5th, 6th, 7th, 8th or higher order polynomial; and/or (ii) the step of comparing the curve with the idealised profile comprises determining the closeness of fit of the curve with the idealised profile; and/or (iii) the step of comparing the curve with the idealised profile comprises determining a first sum which equals the sum of the squares of the differences between the curve and the idealised profile.

The method preferably further comprises determining which first sum indicates the closest fit between a curve and the idealised profile.

The plurality of intensity bins preferably comprises <10, 10-20, 20-30, 30-40, 40-50, 50-60, 60-70, 70-80, 80-90, 90-100 or >100 intensity bins.

According to an embodiment the step of discarding intensity values or values related to the intensity values comprises discarding the intensity values or values related to the intensity values from the highest intensity bin.

According to an embodiment the step of redistributing the remaining intensity values or values related to the intensity values preferably comprises maintaining the number of intensity bins substantially the same. The method preferably further comprises assigning a new reduced intensity range to each of the intensity bins.

According to another aspect of the present invention there is provided an analyser for analysing one or more reagent beads or macrobeads retained or secured in a sample well of a sample plate, the analyser comprising:

one or more devices arranged and adapted:

(i) to obtain an image of a reagent bead or macrobead, the image comprising a plurality of image pixels each having an associated intensity value;

(ii) to distribute the intensity values or values related to the intensity values of the image pixels amongst a plurality of intensity bins and generating an histogram;

(iii) to fit a curve to the histogram;

(iv) to compare the curve with an idealised profile of image pixels which may be expected to be observed if an image of a reagent bead or macrobead which was unaffected by light emanating from neighbouring reagents beads or macrobeads were analysed;

(v) to determine a closeness of fit between the curve and the idealised profile;

(vi) to discard intensity values or values related to the intensity values from one or more of the intensity bins and redistributing the remaining intensity values or values related to the intensity values amongst a plurality of intensity bins and generating a further histogram;

(vii) to repeat steps (iii)-(vi) a plurality of times;

(viii) to determine which curve has the closest fit with the idealised profile; and (ix) to determine the intensity of the reagent bead or macrobead by using or summing the intensity values or values related to the intensity values which were not discarded and which were distributed amongst the plurality of intensity bins which gave the curve having the closest fit with the idealised profile.

According to an aspect of the present invention there is provided a method of analysing one or more reagent beads retained or secured in a sample well of a sample plate, the method comprising:

obtaining an image of a reagent bead, the image comprising a plurality of image pixels each having an associated intensity value;

distributing the intensity values of the image pixels or values related to the intensity values amongst a plurality of intensity bins and generating a first histogram;

fitting a first curve to the first histogram; and comparing the first curve with a standard profile.

According to an embodiment the step of distributing the intensity values comprises:

determining a logarithm of the intensity values; and distributing the logarithm of the intensity values amongst a plurality of intensity bins and generating a first histogram.

According to an embodiment either:

(i) the logarithm comprises a binary, natural or common logarithm; or (ii) the base of the logarithm has a value 2, e or 10; or (iii) the base of the logarithm has a value in the range 2-10 or 10-20 or >20.

The first curve preferably comprises a 4th, 5th, 6th, 7th, 8th or higher order polynomial. However, the equation from any curve-fitting technique may be used. The step of comparing the first curve with the standard profile preferably comprises determining the closeness of fit of the first curve with the standard profile. The step of comparing the first curve with the standard profile preferably comprises determining a first sum which equals the sum of the squares of the differences between the first curve and the standard profile. These differences may be weighted and the preferred weighting is division by the standard deviation of the values of the first curve and the standard curve. However, other embodiments are contemplated wherein a different method of weighting may be used.

The method preferably further comprises:

discarding intensity values or values related to the intensity values for a first time from one or more of the intensity bins and redistributing the remaining intensity values or values related to the intensity values amongst a plurality of intensity bins and generating a second histogram;

fitting a second curve to the second histogram; and comparing the second curve with the standard profile.

The second curve preferably comprises a 4th, 5th, 6th, 7th, 8th or higher order polynomial. The step of comparing the second curve with the standard profile preferably comprises determining the closeness of fit of the second curve with the standard profile. The step of comparing the second curve with the standard profile preferably comprises determining a second sum which equals the sum of the squares of the differences between the second curve and the standard profile.

The method preferably further comprises:

discarding intensity values or values related to the intensity values for a second time from one or more of the intensity bins and redistributing the remaining intensity values or values related to the intensity values amongst a plurality of intensity bins and generating a third histogram;

fitting a third curve to the third histogram; and comparing the third curve with the standard profile.

The third curve preferably comprises a 4th, 5th, 6th, 7th, 8th or higher order polynomial. The step of comparing the third curve with the standard profile preferably comprises determining the closeness of fit of the third curve with the standard profile. The step of comparing the third curve with the standard profile preferably comprises determining a third sum which equals the sum of the squares of the differences between the third curve and the standard profile.

The method preferably further comprises:

discarding intensity values or values related to the intensity values for a third time from one or more of the intensity bins and redistributing the remaining intensity values or values related to the intensity values amongst a plurality of intensity bins and generating a fourth histogram;

fitting a fourth curve to the fourth histogram; and comparing the fourth curve with the standard profile.

The fourth curve preferably comprises a 4th, 5th, 6th, 7th, 8th or higher order polynomial. The step of comparing the fourth curve with the standard profile preferably comprises determining the closeness of fit of the fourth curve with the standard profile. The step of comparing the fourth curve with the standard profile preferably comprises determining a fourth sum which equals the sum of the squares of the differences between the fourth curve and the standard profile.

The method preferably further comprises:

discarding intensity values or values related to the intensity values for a $n-1^{th}$ time from the one or more intensity bins and redistributing the remaining intensity values or values related to the intensity values amongst a plurality of intensity bins and generating an $n^{th}$ histogram;

fitting a $n^{th}$ curve to the $n^{th}$ histogram; and comparing the $n^{th}$ curve with the standard profile;

wherein n is selected from the group consisting of: 5, 6, 7, 8, 9, 10, 11, 12, 13, 14, 15, 16, 17, 18, 19, 20, 21, 22, 23, 24, 25, 26, 27, 28, 29, 30 or >30.

The $n^{th}$ curve preferably comprises a 4th, 5th, 6th, 7th, 8th or higher order polynomial. The step of comparing the $n^{th}$ curve with the standard profile preferably comprises determining the closeness of fit of the $n^{th}$ curve with the standard profile. The step of comparing the $n^{th}$ curve with the standard profile preferably comprises determining a $n^{th}$ sum which equals the sum of the squares of the differences between the $n^{th}$ curve and the standard profile.

The plurality of intensity bins preferably comprises <10, 10-20, 20-30, 30-40, 40-50, 50-60, 60-70, 70-80, 80-90, 90-100 or >100 intensity bins.

The method preferably further comprises determining which of the first sum and/or the second sum and/or the third sum and/or the fourth sum and/or the $n^{th}$ sum have the lowest value or have a value which otherwise indicates the closest fit between the first curve, the second curve, the third curve, the fourth curve or the $n^{th}$ curve and the standard profile.

The method preferably further comprises determining the intensity of the reagent bead by using or summing the intensity values or values related to the intensity values which were not discarded and which were distributed amongst the plurality of intensity bins which gave the curve having the closest fit to the standard profile.

The standard profile preferably comprises a profile which corresponds with the expected intensity profile of a reagent bead being analysed wherein the reagent bead being analysed is not significantly affected by stray reflections from one or more neighbouring reagent beads, indirect reflections from high signal beads from the sample well wall or from reagent bead surface abnormalities.

The preferred profile is comprised of a plurality of reagent averaged bead image profiles that fit this criteria. A family of standard profiles may be established based on the range of the average intensity values for the reagent bead signal. The preferred standard profile against which the profile of the reagent bead should be compared is based on the average intensity value of that reagent bead. The standard profile to be used is preferably the one whose range includes the average value of the reagent bead.

According to another aspect of the present invention there is provided an analyser for analysing one or more reagent beads retained or secured in a sample well of a sample plate, the analyser comprising:

a device arranged and adapted to obtain an image of a reagent bead, the image comprising a plurality of image pixels each having an associated intensity value;

a device arranged and adapted to distribute the intensity values or values related to the intensity values of the image pixels amongst a plurality of intensity bins and to generate a first histogram;

a device arranged and adapted to fit a first curve to the first histogram; and a device arranged and adapted to compare the first curve with a standard profile.

According to another aspect of the present invention there is provided a method of analysing one or more reagent beads retained or secured in a sample well of a sample plate, the method comprising:

(i) obtaining an image of a reagent bead, the image comprising a plurality of image pixels each having an associated intensity value;

(ii) distributing the intensity values or values related to the intensity values of the image pixels amongst a plurality of intensity bins and generating an histogram;

(iii) fitting a curve to the histogram;

(iv) comparing the curve with a standard profile to determine a closeness of fit between the curve and the standard profile;

(v) discarding intensity values or values related to the intensity values from one or more of the intensity bins and redistributing the remaining intensity values or values related to the intensity values amongst a plurality of intensity bins and generating an histogram;

(vi) repeating steps (iii)-(v) a plurality of times;

(vii) determining which curve has the closest fit with the standard profile; and (viii) determining the intensity of the reagent bead by using or summing the intensity values or values related to the intensity values which were not discarded and which were distributed amongst the plurality of intensity bins which gave the curve having the closest fit with the standard profile.

According to another aspect of the present invention there is provided an analyser for analysing one or more reagent beads retained or secured in a sample well of a sample plate, the analyser further comprising a control system which is arranged and adapted:

(i) to obtain an image of a reagent bead, the image comprising a plurality of image pixels each having an associated intensity value;

(ii) to distribute the intensity values or values related to the intensity values of the image pixels amongst a plurality of intensity bins and to generate an histogram;

(iii) to fit a curve to the histogram;

(iv) to compare the curve with a standard profile to determine a closeness of fit between the curve and the standard profile;

(v) to discard intensity values or values related to the intensity values from one or more of the intensity bins, to redistribute the remaining intensity values or values related to the intensity values amongst a plurality of intensity bins and to generate an histogram;

(vi) to repeat steps (iii)-(v) a plurality of times;

(vii) to determine which curve has the closest fit with the standard profile; and (viii) to determine the intensity of the reagent bead by using or summing the intensity values or values related to the intensity values which were not discarded and which were distributed amongst the plurality of intensity bins which gave the curve having the closest fit with the standard profile.

According to another aspect of the present invention there is provided a method of analysing a reagent bead retained or secured in a sample well of a sample plate comprising:

obtaining an image of a reagent bead, the image comprising a plurality of image pixels each having an associated intensity value; and discarding the intensity values or values related to the intensity values of image pixels which are determined to be affected by stray reflections from another reagent bead in the sample well.

According to another aspect of the present invention there is provided an analyser for analysing a reagent bead retained or secured in a sample well of a sample plate, the analyser comprising:

a device arranged and adapted to obtain an image of a reagent bead, the image comprising a plurality of image pixels each having an associated intensity value; and a device arranged and adapted to discard the intensity values or values related to the intensity values of image pixels which are determined to be affected by stray reflections from another reagent bead in the sample well.

According to an aspect of the present invention there is provided a method of analysing one or more reagent beads retained or secured in a sample well of a sample plate, the method comprising:

obtaining an image of a reagent bead, the image comprising a plurality of image pixels each having an associated intensity value;

distributing a logarithm of the intensity values of the image pixels amongst a plurality of intensity bins and generating a first histogram;

fitting a first curve to the first histogram; and comparing the first curve with a standard profile.

According to an aspect of the present invention there is provided an analyser for analysing one or more reagent beads retained or secured in a sample well of a sample plate, the analyser comprising:

a device arranged and adapted to obtain an image of a reagent bead, the image comprising a plurality of image pixels each having an associated intensity value;

a device arranged and adapted to distribute a logarithm of the intensity values of the image pixels amongst a plurality of intensity bins and to generate a first histogram;

a device arranged and adapted to fit a first curve to the first histogram; and a device arranged and adapted to compare the first curve with a standard profile.

BRIEF DESCRIPTION OF THE DRAWINGS

Various embodiments of the present invention will now be described, by way of example only, and with reference to the accompanying drawings in which.

DETAILED DESCRIPTION OF THE INVENTION

A preferred embodiment of the present invention will now be described which relates generally to a method and apparatus for analysing reagent beads located in a sample well of a sample plate and which is concerned with the problem of reducing crosstalk.

The reagent beads are evenly coated with a reagent and include a chemiluminescent, fluorescent or chromogenic indicator. The intensity of light emanating from a reagent bead gives a measure of the strength of the reaction of the reagent on the reagent bead with the sample dispensed into the sample well.

The sample well being analysed preferably comprises ten recesses or through holes in which reagent beads are secured or retained. During an earlier stage of the procedure a sample will have been dispensed into the sample well so as to cover the reagent beads such that the different reagent beads may react with the sample.

During the analysis stage, if a reagent bead is not subject to stray reflections from light emanating from a neighbouring reagent bead then the intensity (or logarithm of intensity) profile of image pixels which together form an image of the light emanating from a reagent bead should exhibit a characteristic profile of light output which should correspond with an idealised profile. Any light which is reflected off the walls of the sample well or through bead surface abnormalities may also be considered.

According to the preferred embodiment images from reagent beads which are not affected by light emanating from a neighbouring reagent bead are obtained. The image of a reagent bead preferably comprises a plurality of image pixels which may have different intensities. The intensities of the image pixels are then processed by distributing either the intensity values or alternatively the logarithm of the intensity values amongst a plurality of intensity bins and an idealised profile is generated. The idealised profile corresponds with the intensity (or logarithm of intensity) distribution of image pixels which may be expected when analysing a reagent bead which is not affected by light emanating from a neighbouring reagent bead.

If an intensity (or logarithm of intensity) profile of the image pixels of a particular reagent bead is observed to deviate significantly from the idealised profile then this is due to light emanating from a neighbouring reagent bead which reflects off the particular reagent bead. Significant deviations can be observed if a neighbouring reagent bead has reacted strongly and emanates a relatively high intensity of light.

According to the preferred embodiment an idealised intensity (or logarithm of intensity) profile is constructed from an histogram comprised of the intensity values (or the logarithm of the intensity values) of image pixels which together make up an image of a reagent bead which falls within a cell boundary and wherein the reagent bead is not affected by stray reflections from a neighbouring reagent bead.

Figure 1:
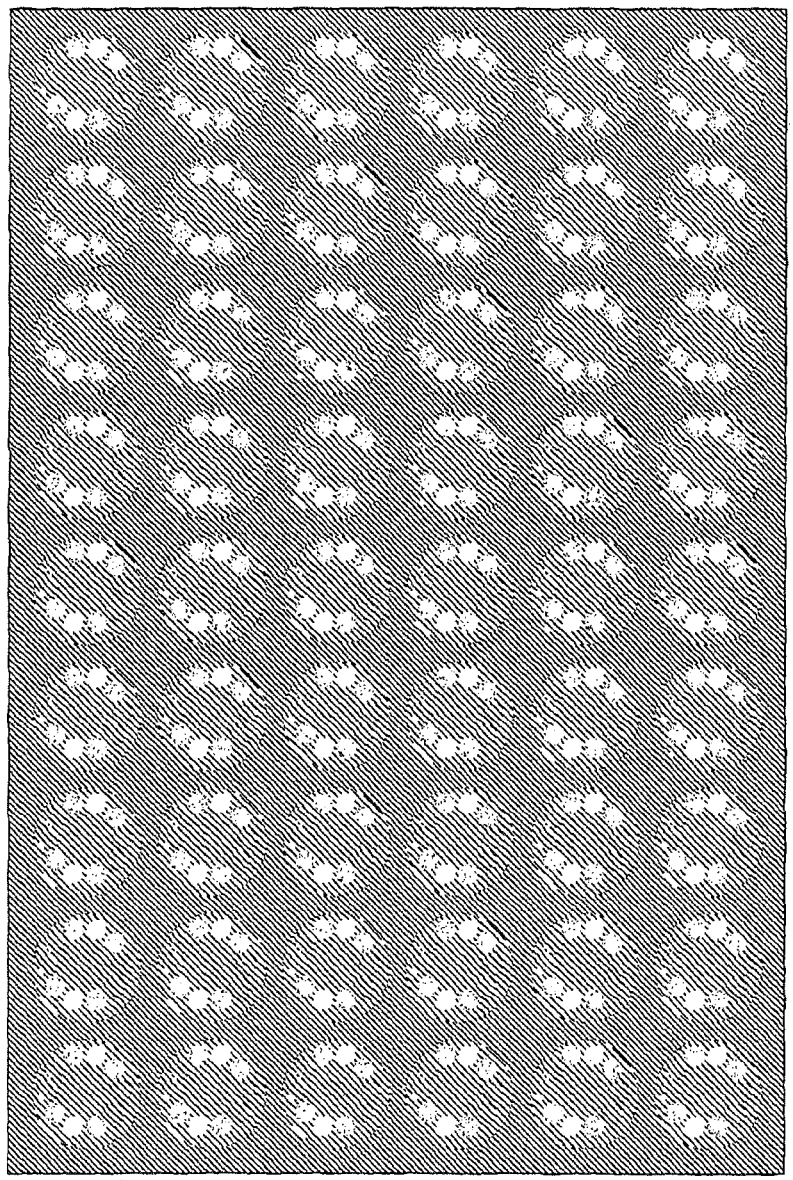
FIG. 1 shows an image of a 9×6 array of sample wells during an analysis stage wherein each sample well comprises ten reagent beads arranged in a ring around the base of the sample well and wherein two of the reagent beads in each sample well emit light with a relatively high intensity.
Figure 2:
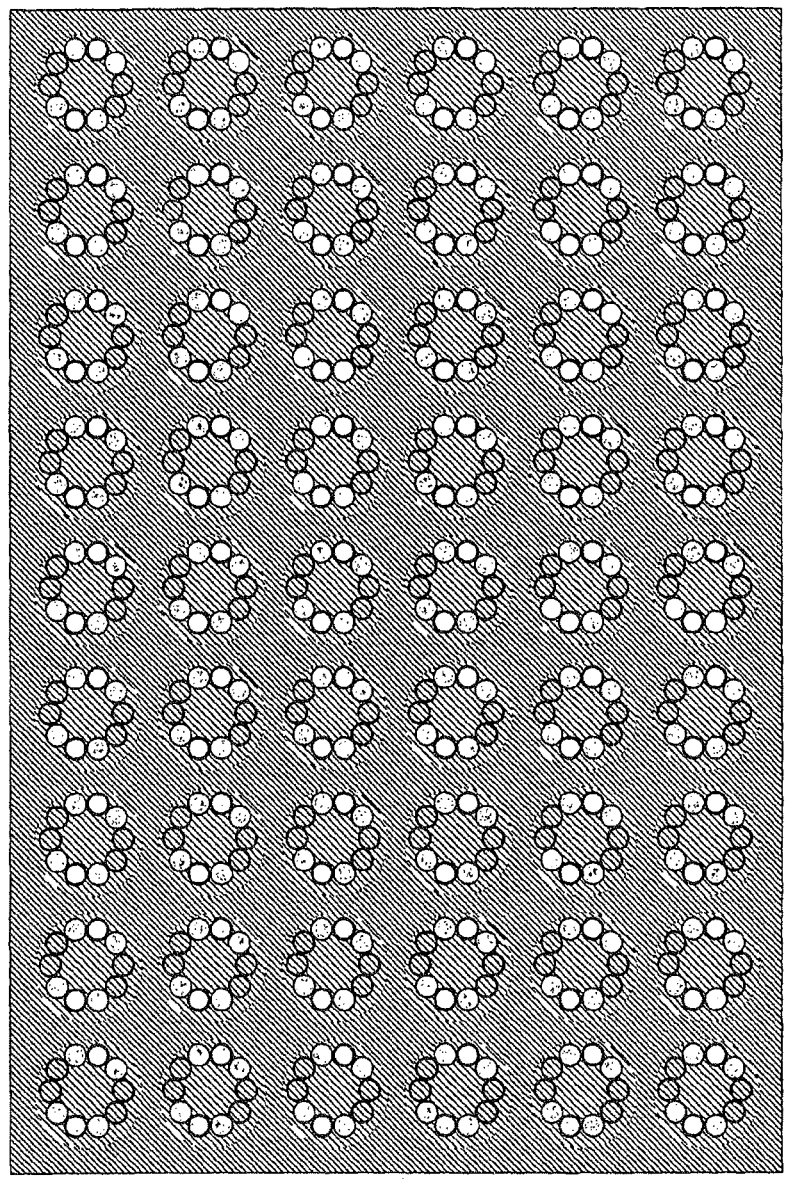
FIG. 2 shows how the imaging system according to the preferred embodiment defines ten circular cell boundaries for each sample well to define the position of ten reagent beads which are secured within the base portion of each sample well.

FIG. 2 shows how the imaging system according to the preferred embodiment superimposes ten cell boundaries for each sample well. The superimposed cell boundaries are used to define the position (and intensity) of reagent beads located within a sample well.

Figure 3:
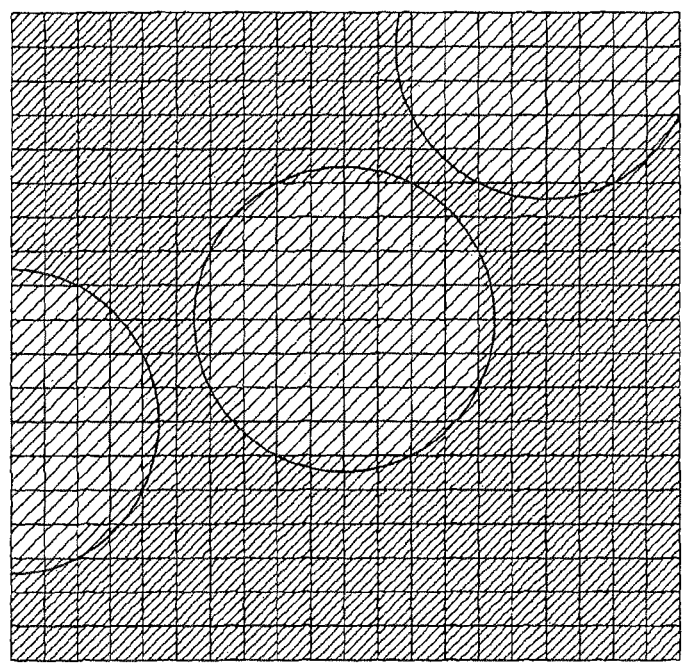
FIG. 3 shows in greater detail a cell boundary which is superimposed upon the image of a reagent bead located in a sample well and wherein the image of the reagent bead is comprised of a plurality of image pixels wherein the intensity of the image pixels is not substantially distorted by reflections of light emanating from neighbouring reagent beads.

FIG. 3 shows in greater detail a cell boundary which is superimposed upon the image of a reagent bead located in a sample well. The image is comprised of a plurality of pixels wherein the intensity of the image pixels are not distorted by light emanating from neighbouring reagent beads.

Figure 4:
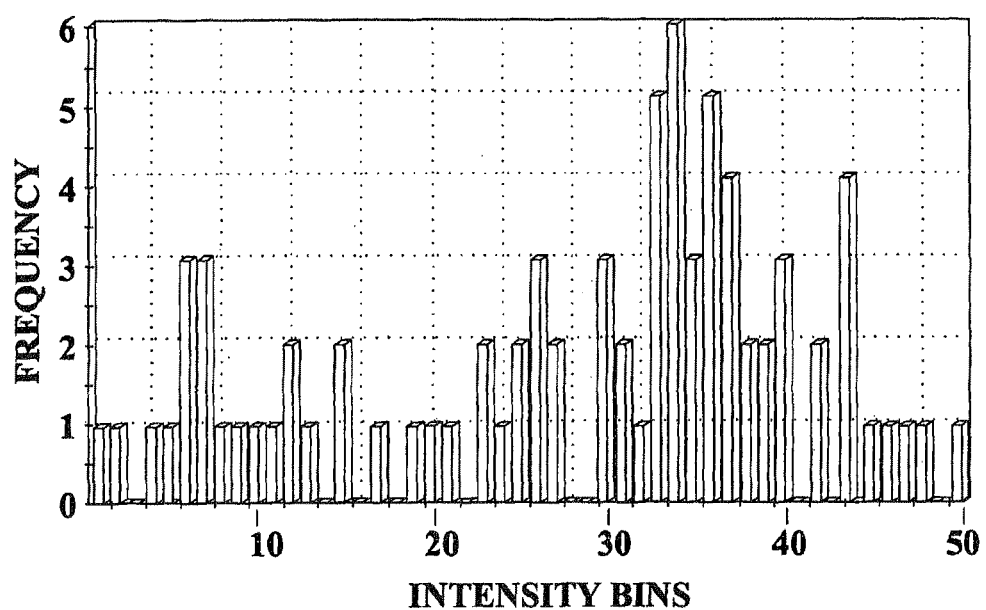
FIG. 4 shows an histogram of the intensity of 80 image pixels within a cell boundary and wherein the intensity of the 80 image pixels have been distributed amongst 50 intensity bins.

The intensity of the image pixels (or alternatively the logarithm of the intensity values of the image pixels) within a cell boundary are distributed amongst a plurality of intensity bins and an histogram of the frequency of the intensity (or logarithm of intensity) of the image pixels is constructed. FIG. 4 shows an example of an histogram of the intensity values of 80 image pixels within a cell boundary. The intensity values of the 80 image pixels are shown distributed amongst 50 intensity bins. It will be understood by those skilled in the art that other embodiments are contemplated wherein the number of image pixels may be <80 or >80. It will also be understood by those skilled in the art that other embodiments are contemplated wherein the number of intensity bins may be <50 or >50.

Figure 5:
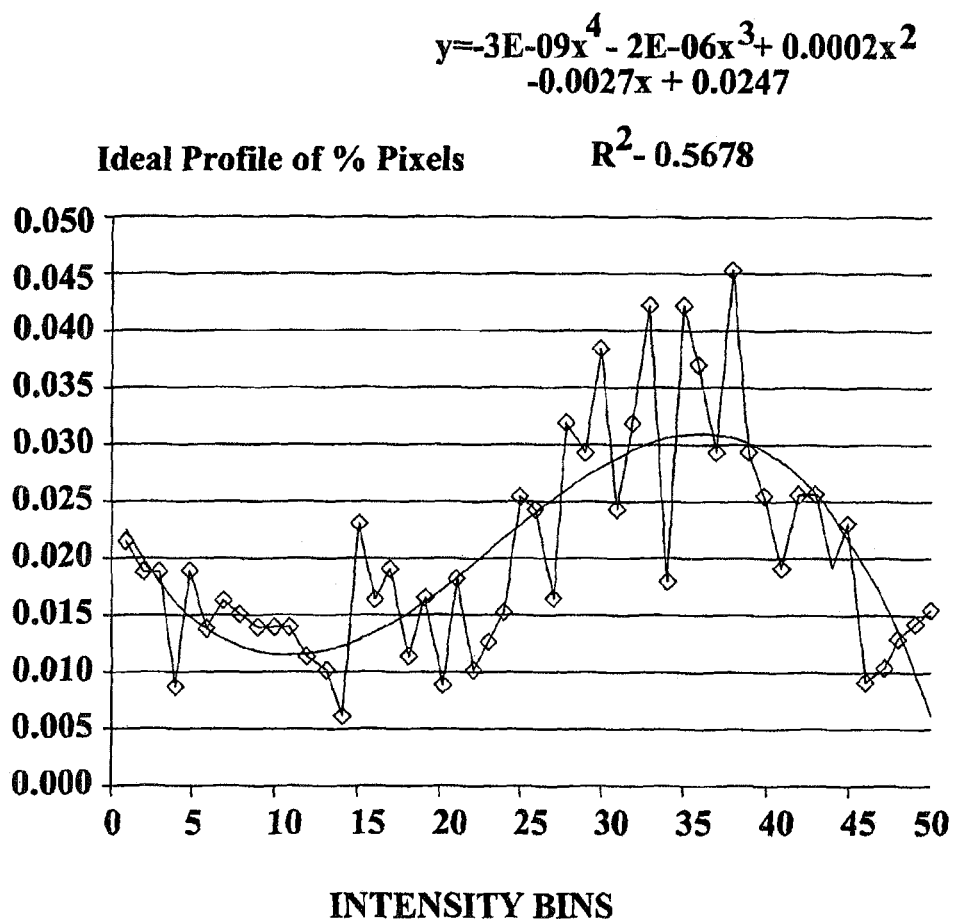
FIG. 5 shows a curve superimposed upon the histogram of the intensity of image pixels shown in FIG. 4.

According to the preferred embodiment multiple histogram profiles from a plurality of beads which are unaffected by stray reflections from neighbouring reagent beads are averaged. An histogram of the intensity (or logarithm of the intensity) profile of image pixels which may be expected to be observed when analysing an image of a reagent bead which is unaffected by light emanating from neighbouring reagent beads is then constructed. Once an histogram has been constructed, then according to the preferred embodiment a 4th (or higher order) polynomial curve is preferably fitted to the histogram so that an idealised profile relating to the distribution of the intensity values (or logarithm of intensity values) of the image pixels is then produced. FIG. 5 shows an example of a polynomial curve which has been fitted to an histogram of the intensities of image pixels. The curve is stored or retained as an idealised profile.

In the particular example shown in FIG. 5 the polynomial curve which is fitted follows the relationship:

$$y=-3\times10^{-9}x^4-2\times10^{-6}x^3+0.0002x^2-0.0027x+0.0247 \quad (1)$$

The "y" value shown in FIG. 5 is the percentage of pixel values which fall into a particular intensity bin.

Embodiments are contemplated wherein a family of curves may be derived if the ideal or idealised profile changes over the intensity range of the image pixels.

The characterization of an ideal or idealised profile may be performed individually for a macroarrayer as there may be slight variations in the optics, other components between instruments, coating characteristics or assay chemistry. As a result, the idealised profile may vary slightly from instrument to instrument and assay to assay. Alternatively, instruments may use a generic ideal or idealised profile.

Once an idealised profile for a particular instrument has been derived or is otherwise acquired, then when a sample plate is analysed an histogram of the intensity (or the logarithm of the intensity) of image pixels of a reagent bead is preferably obtained. A polynomial curve is then preferably fitted to the histogram and the curve is preferably compared against the idealised profile curve. A determination is preferably made as to how close the correspondence is between the curve and the idealised profile. According to the preferred embodiment the sum of the squares of the differences between points on an ideal or idealised curve and corresponding points on a curve which is fitted to the histogram of the intensity (or logarithm of the intensity) of image pixels being analysed is preferably calculated.

Figure 6:
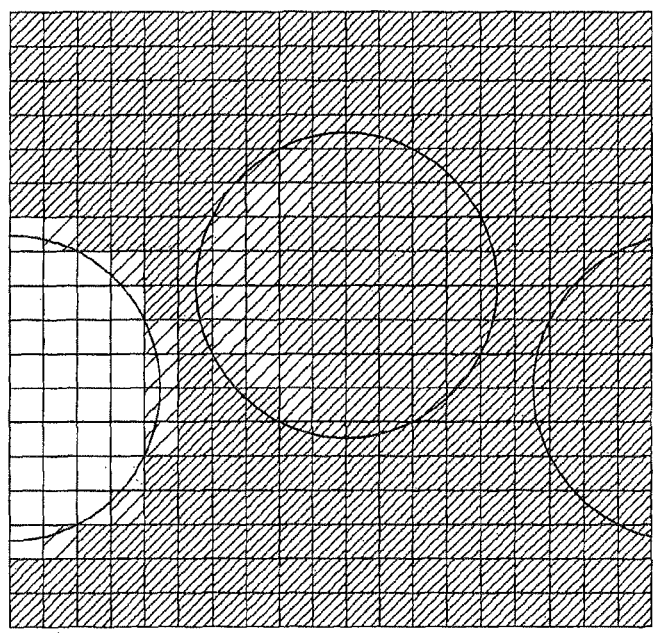
FIG. 6 shows a pixellated image of a reagent bead wherein some of the image pixels are affected by light emanating from an adjacent reagent bead which has a relatively high luminescence or fluorescence.

FIG. 6 shows an example of a pixelated image of a particular reagent bead. Signal emanating from an adjacent high signal bead is reflected off a portion of the particular reagent bead back towards the camera detector or imaging sensor and hence the intensity of some of the image pixels is distorted or otherwise affected due to stray light. The reagent bead shown in the centre of FIG. 6 is located close to a reagent bead to the left which strongly emits light. Light from the reagent bead to the left will reflect off the reagent bead shown in the centre.

Figure 7:
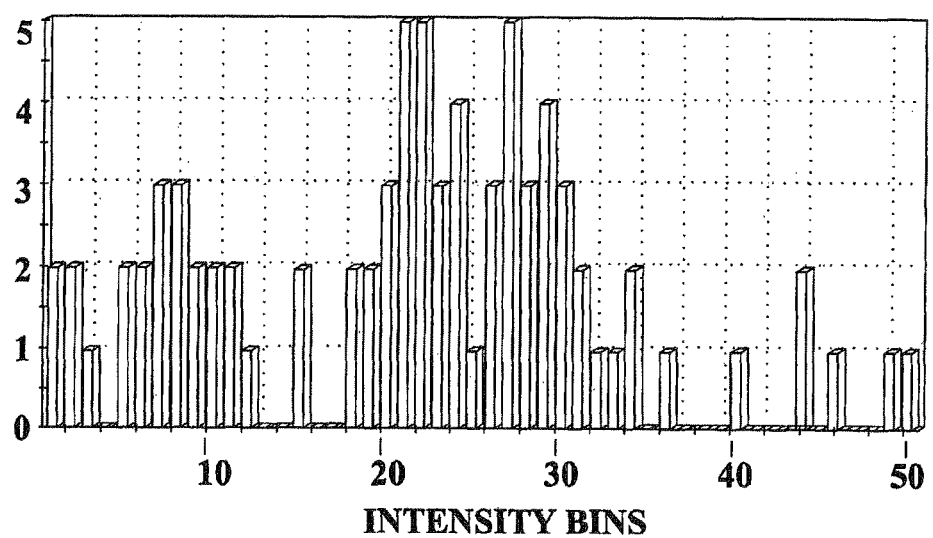
FIG. 7 shows an histogram of the intensity of 80 image pixels within a cell boundary and wherein the intensity of the 80 image pixels have been distributed amongst 50 intensity bins and wherein the image is comprised of a plurality of pixels wherein the intensity of some of the image pixels is affected by light emanating from a neighbouring reagent bead.

FIG. 7 shows an histogram of the intensity of 80 image pixels which together form an image of the reagent bead shown in the centre of FIG. 6 within the cell boundary shown. The intensity values of the image pixels are distributed amongst 50 intensity bins.

According to the preferred embodiment a control system preferably eliminates or discards the intensity values (or the logarithm of the intensity values) in the highest intensity bin (intensity bin #50) and the remaining intensity data is then preferably redistributed amongst a new set of e.g. 50 intensity bins and a new histogram is obtained. According to an embodiment a 6th order polynomial curve is fitted to the new histogram and the resulting curve is then preferably compared to the idealised curve. A determination of the goodness of fit is then made preferably by determining the squares of the differences between the curve and the idealised profile.

This process is preferably repeated multiple times and each time the intensity (or the logarithm of the intensity) values in the highest intensity bin (e.g. intensity bin #50) are preferably discarded and the remaining intensity (or logarithm of intensity) data is preferably redistributed amongst a new set of intensity bins.

According to an embodiment this process may be repeated until intensity data has been discarded from the highest intensity bin x times, wherein x corresponds to 50% of the total number of intensity bins.

According to the preferred embodiment the profile or curve which has the lowest value for the sum of the squared differences between the curve and the idealised profile is preferably taken to represent image data which is substantially undistorted by light emanating from neighbouring reagent beads. The intensity (or the logarithm of the intensity) of the image pixels corresponding to the intensity data which produces the best fit with the idealised profile may, for example, be summed to give a determination of the undistorted intensity of the reagent bead.

It can be seen from FIG. 7 that there are several high intensity pixels falling within the 40th, 44th, 46th, 49th and 50th intensity bins that appear to be anomalous.

Figure 8:
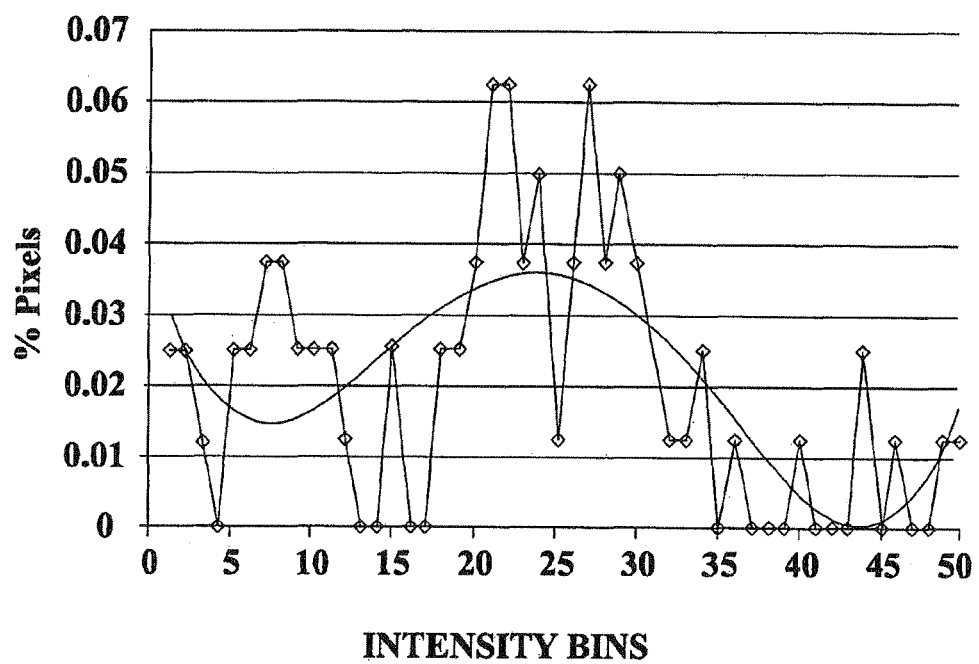
FIG. 8 shows a curve superimposed upon the histogram of the intensity of image pixels shown in FIG. 7.

FIG. 8 shows a 4th order polynomial curve which is initially fitted to the histogram shown in FIG. 7.

The number of pixels in each intensity bin are preferably converted to a percentage of all the pixels since as intensity data is eliminated from intensity bins one at a time, then less image pixels are considered. After the image pixel data in the highest intensity bin is eliminated or discarded, the remaining image pixel data is distributed into a new 50-bin histogram for the next iteration.

Figure 9:
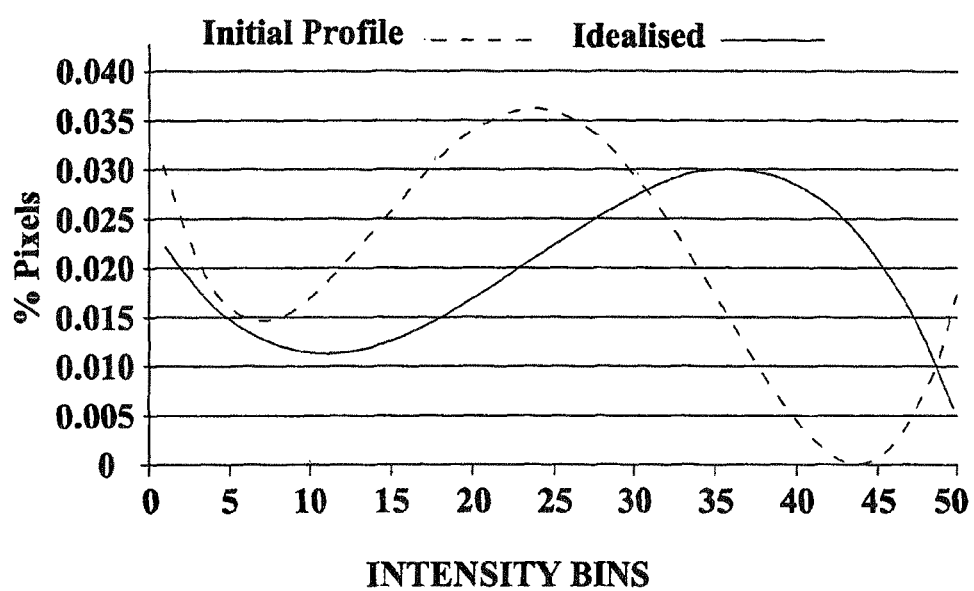
FIG. 9 shows a comparison of the curve shown in FIG. 8 with an idealised profile as shown in FIG. 5.

As can be seen from FIG. 9, the curve which is initially fitted to the histogram shown in FIG. 7 does not match the idealised profile particularly closely.

Figure 10:
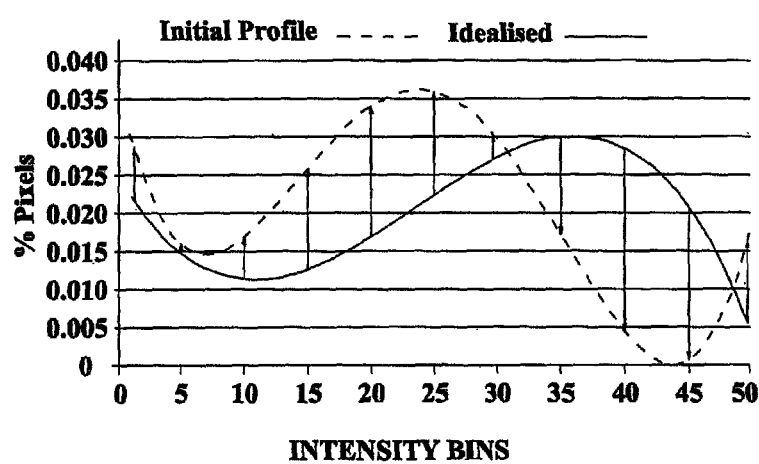
FIG. 10 illustrates how a measure of the difference between the curve shown in FIG. 8 and the idealised profile shown in FIG. 5 may be calculated by determining the squares of the differences between the two curves.

FIG. 10 shows how according to an embodiment of the present invention squaring the difference between the profile or curve fit to an histogram and the idealised profile enables an index value for the goodness of fit to be obtained.

Figure 11:
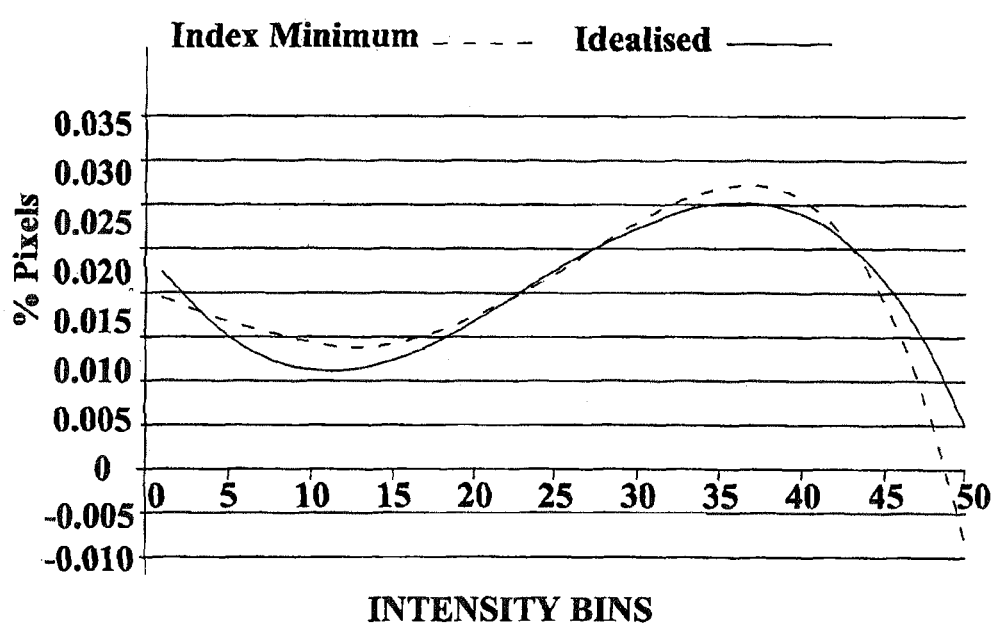
FIG. 11 shows a curve obtained according to an embodiment of the present invention which is determined to have the best fit with the idealised profile shown in FIG. 5.

In the particular example shown and described above with reference to FIG. 7, the intensity bin profile with the lowest value of the sum of the squared difference (Index Minimum) was derived from the image pixels that were initially distributed in the first 37 intensity bins. The profile comparison between this intensity data and the idealised profile is shown in FIG. 11.

Using just the intensity values of the image pixels from the first 37 intensity bins results in an average pixel value that substantially matches the values for other reagent beads that were identical in preparation but which were not located in a sample well adjacent to a reagent bead which emitted a relatively high intensity of light.

Figure 12:
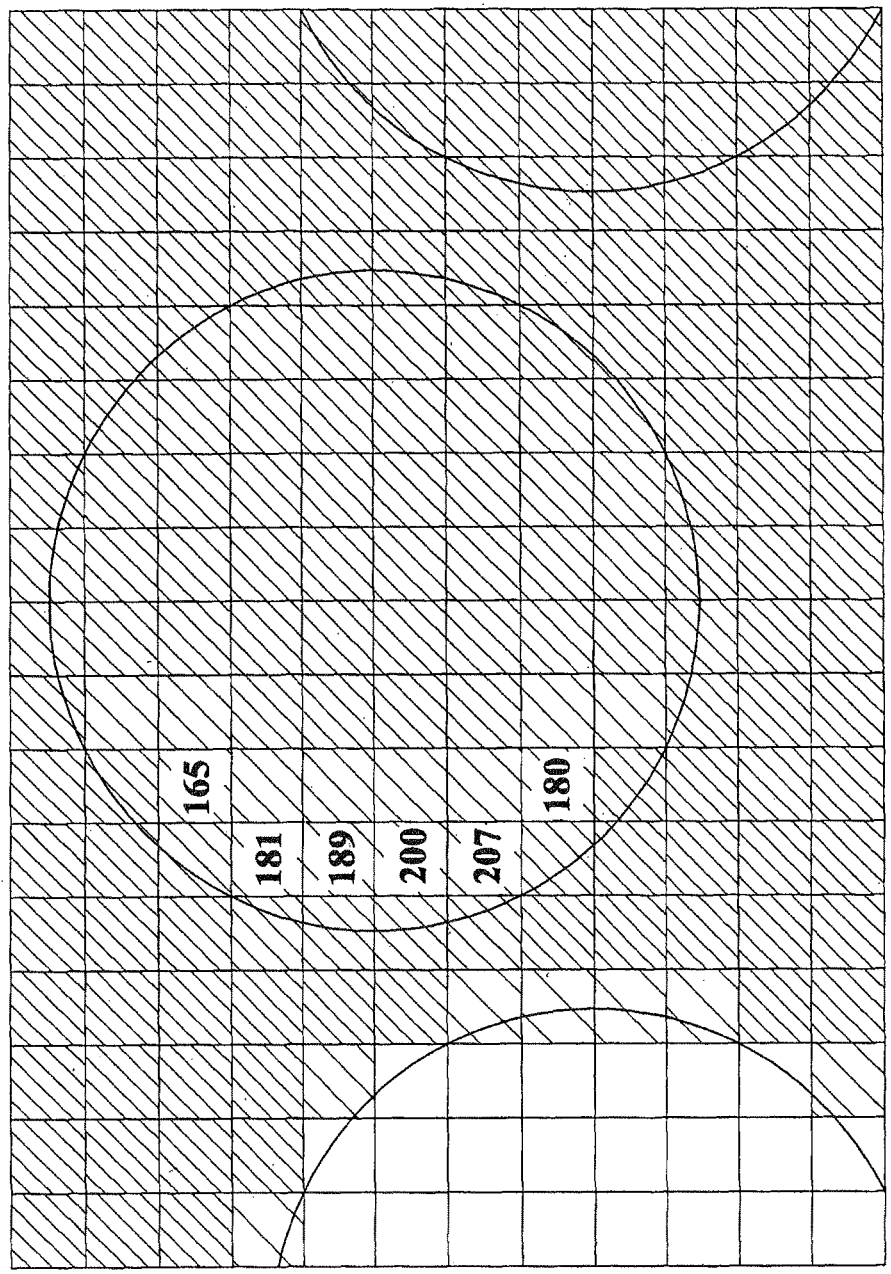
FIG. 12 shows image pixels which are flagged as being affected by light emanating from a neighbouring reagent bead and which according to the preferred embodiment are discarded when determining the overall intensity of the reagent bead.

Some image pixels are shown in FIG. 12 together with their Relative Luminescence Unit ("RLU") values. The six image pixels highlighted are those image pixels which were eliminated from consideration when determining the overall intensity of the reagent bead. It can be seen that these image pixels correspond to the surface area of the reagent bead being analysed which is most likely to be affected by light reflected from the adjacent reagent bead which is emitting a relatively high intensity of light. According to this particular example, the average Relative Luminescence Unit of all the image pixels was reduced from 86.5 to 79.1.

Figure 13A:
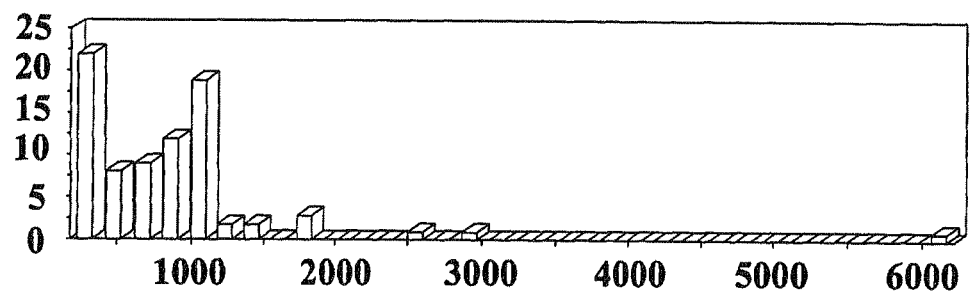
FIG. 13A shows a histogram showing the distribution of 80 pixels relating to an image of a reagent bead distributed amongst 32 intensity bins and FIG. 13B a histogram after having applied a crosstalk algorithm according to an embodiment of the present invention wherein 10 pixels have been rejected and the remaining 70 pixels are shown distributed amongst 32 intensity bins.
Figure 13B:
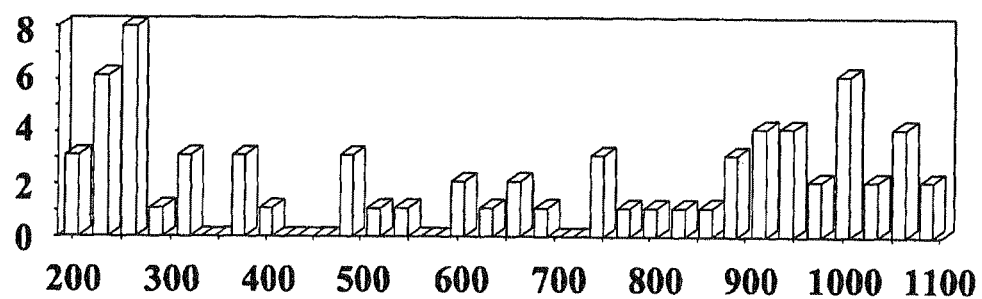

FIG. 13A shows a histogram showing the distribution of 80 pixels relating to an image of a reagent bead distributed amongst 32 intensity bins. In this particular example the net intensity (mean) is 831.112. FIG. 13B shows a histogram after having applied a crosstalk algorithm according to an embodiment of the present invention wherein a total of ten pixels have been rejected (two pixels from intensity bins #6 and #7, three pixels from intensity bin #9 and one pixel from intensity bins #13, #15 and #32). The remaining 70 pixels are shown distributed amongst 32 intensity bins. In this particular example the net intensity (mean) is now reduced to 638.000.

Although the present invention has been described with reference to preferred embodiments, it will be understood by those skilled in the art that various changes in form and detail may be made without departing from the scope of the invention as set forth in the accompanying claims.

The invention claimed is:

1. A method of analysing one or more reagent beads or macrobeads retained or secured in a sample well of a sample plate, said method comprising:
   (i) obtaining an image of the one or more reagent beads or macrobeads retained or secured in the sample well of the sample plate, said image comprising a plurality of image pixels each having an associated intensity value;
   (ii) distributing the intensity values or values related to said intensity values of said image pixels amongst a plurality of intensity bins and generating an histogram;
   (iii) fitting a curve to said histogram;
   (iv) comparing said curve with an idealised profile of image pixels expected to be observed if an image of a reagent bead or macrobead which was unaffected by light emanating from neighbouring reagents beads or macrobeads was analysed;
   (v) determining a closeness of fit between said curve and said idealised profile;
   (vi) discarding intensity values or values related to said intensity values from the highest intensity bin and redistributing the remaining intensity values or values related to said intensity values amongst a plurality of intensity bins and generating a further histogram, wherein said step of redistributing said remaining intensity values or values related to said intensity values comprises maintaining the number of intensity bins substantially the same and assigning a new reduced intensity range to each of the intensity bins;
   (vii) repeating steps (iii)-(vi) a plurality of times;
   (viii) determining which curve has the closest fit with said idealised profile; and
   (ix) determining the intensity of said reagent bead or macrobead by summing the intensity values or values related to said intensity values which were not discarded and which were distributed amongst said plurality of intensity bins which gave the curve having the closest fit with said idealised profile.

2. The method as claimed in claim 1, wherein said step of distributing the intensity values comprises:
   determining a logarithm of said intensity values; and
   distributing the logarithm of said intensity values amongst a plurality of intensity bins and generating a first histogram.

3. The method as claimed in claim 2, wherein either:
   (i) said logarithm comprises a binary, natural or common logarithm; or
   (ii) the base of said logarithm has a value 2, e or 10; or
   (iii) the base of said logarithm has a value in the range 2-10 or 10-20 or >20.

4. The method as claimed in claim 3, wherein:
   (i) said curve comprises a 4th, 5th, 6th, 7th, 8th or higher order polynomial; and/or
   (ii) the step of comparing said curve with said idealised profile comprises determining the closeness of fit of said curve with said idealised profile; and/or
   (iii) the step of comparing said curve with said idealised profile comprises determining a first sum which equals the sum of the squares of the differences between said curve and said idealised profile.

5. The method as claimed in claim 2, wherein:
   (i) said curve comprises a 4th, 5th, 6th, 7th, 8th or higher order polynomial; and/or
   (ii) the step of comparing said curve with said idealised profile comprises determining the closeness of fit of said curve with said idealised profile; and/or
   (iii) the step of comparing said curve with said idealised profile comprises determining a first sum which equals the sum of the squares of the differences between said curve and said idealised profile.

6. The method as claimed in claim 1, wherein:
   (i) said curve comprises a 4th, 5th, 6th, 7th, 8th or higher order polynomial; and/or
   (ii) the step of comparing said curve with said idealised profile comprises determining the closeness of fit of said curve with said idealised profile; and/or
   (iii) the step of comparing said curve with said idealised profile comprises determining a first sum which equals the sum of the squares of the differences between said curve and said idealised profile.

7. The method as claimed in claim 6, further comprising determining which first sum indicates the closest fit between a curve and said idealised profile.

8. The method as claimed in claim 1, wherein said plurality of intensity bins comprises <10, 10-20, 20-30, 30-40, 40-50, 50-60, 60-70, 70-80, 80-90, 90-100 or >100 intensity bins.

* * * * *